(12) United States Patent
Sweitzer

(10) Patent No.: US 11,660,210 B2
(45) Date of Patent: May 30, 2023

(54) IMPLANT EXTRACTOR ASSEMBLY AND METHOD OF IMPLANT EXTRACTION

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 126 days.

(21) Appl. No.: 16/834,531

(22) Filed: Mar. 30, 2020

(65) Prior Publication Data
US 2021/0093468 A1 Apr. 1, 2021

Related U.S. Application Data

(60) Provisional application No. 62/908,223, filed on Sep. 30, 2019.

(51) Int. Cl.
A61B 17/92 (2006.01)
A61F 2/46 (2006.01)

(52) U.S. Cl.
CPC .......... *A61F 2/4612* (2013.01); *A61B 17/921* (2013.01); A61F 2002/4619 (2013.01); A61F 2002/4628 (2013.01)

(58) Field of Classification Search
CPC ........ A61F 2002/4619; A61F 2002/462; A61F 2/4612; A61F 2/4605; A61F 2/4606; A61F 2/4607; A61F 2/4603; A61F 2/46; A61B 17/921; A61B 17/92
See application file for complete search history.

(56) References Cited

U.S. PATENT DOCUMENTS

| 4,222,382 A | 9/1980 | Antonsson et al. |
| D279,405 S | 6/1985 | Lentz |
| 4,993,410 A * | 2/1991 | Kimsey ................. A61F 2/4607 606/100 |
| 5,196,018 A | 3/1993 | Willert et al. |
| 6,709,439 B2 * | 3/2004 | Rogers .................. A61B 17/92 606/86 R |
| 9,456,828 B2 | 10/2016 | Kerboul et al. |
| D808,531 S | 1/2018 | Slater |

(Continued)

FOREIGN PATENT DOCUMENTS

| EP | 0788773 A1 * | 5/1997 | .......... A61F 2/4603 |
| EP | 0788773 A1 * | 8/1997 | ......... A61B 17/1659 |
| FR | 2794642 A1 | 12/2000 | |

OTHER PUBLICATIONS

English translation of EP-0788773-A1, machine generated Dec. 10, 20210 via https://worldwide.espacenet.com/publicationDetails/description?CC=EP&NR=0788773A1&KC=A1&FT=D&ND=3&date=19970813&DB=&locale=en_EP# (Year: 2021).*

(Continued)

*Primary Examiner* — Amy R Sipp
(74) *Attorney, Agent, or Firm* — Kim IP Law Group LLC

(57) ABSTRACT

An implant extractor assembly that includes a handle, and a mount connectable to the handle. The mount includes a main body, a quick connect about a proximal end of the main body, and an L-shaped connector about a distal end of the main body. The L-shaped connector includes a through hole having a longitudinal axis transverse to a longitudinal axis of the main body.

24 Claims, 17 Drawing Sheets

(56) References Cited

U.S. PATENT DOCUMENTS

| | | |
|---|---|---|
| 10,398,569 B2 | 9/2019 | Jaumard |
| 10,456,270 B2 | 10/2019 | Slater |
| 2009/0112219 A1* | 4/2009 | Daniels ................ A61F 2/4637 606/99 |
| 2012/0290099 A1 | 11/2012 | Gibson et al. |
| 2018/0042734 A1 | 2/2018 | Slater |
| 2020/0214853 A1 | 7/2020 | Sweitzer |
| 2021/0093468 A1 | 4/2021 | Sweitzer |
| 2021/0228378 A1* | 7/2021 | Atkin .................... A61F 2/4607 |

OTHER PUBLICATIONS

Machine translation of EP-0788773-A1. (Year: 2021).*
International Search Report and Written Opinion of the International Searching Authority, PCT/US2020/050878, dated Nov. 19, 2020.

* cited by examiner

IMPLANT EXTRACTOR ASSEMBLY AND METHOD OF IMPLANT EXTRACTION

BACKGROUND OF THE DISCLOSURE

Exemplary embodiments of the subject disclosure relate generally to the field of medical device implant extraction tools. Specifically, the subject disclosure relates to an implant extraction tool for extracting orthopedic implants implanted into bone.

SUMMARY OF THE DISCLOSURE

In accordance with an exemplary embodiment, the subject disclosure provides an implant extractor assembly that includes a handle, and a mount connectable to the handle. The mount includes a main body, a quick connect about a proximal end of the main body, and an L-shaped connector about a distal end of the main body. The L-shaped connector includes a through hole having a longitudinal axis transverse to a longitudinal axis of the main body.

In one embodiment, a through hole is positioned along the longitudinal axis of the main body. The implant extractor assembly can further include a fastener for extending through the though hole. In one embodiment, the longitudinal axis of the through hole is at an angle of about 20° to 50° from the longitudinal axis of the main body. In one embodiment, a longitudinal axis of the handle is parallel to, or coaxial to, a longitudinal axis of the main body. The handle can, in certain embodiments, include a cooperating quick connect for operatively engaging the quick connect of the main body.

In one embodiment, the implant extraction assembly further includes a strike plate extendable from the mount. In certain embodiments, the strike plate extends substantially perpendicular to the longitudinal axis of the main body. The main body can include a pair of opposing flats adjacent the quick connect for engaging the strike plate, and/or a plateau for engaging the strike plate, and/or a mounting head for receiving the strike plate, such as a polygonal shaped mounting head.

In accordance with another exemplary embodiment, the subject disclosure provides a mount for an implant extractor assembly that includes a main body, a quick connect about a proximal end of the main body, and an L-shaped connector about a distal end of the main body, the L-shaped connector includes a through hole having a longitudinal axis transverse to a longitudinal axis of the main body.

In one embodiment, the mount further includes a mounting head adjacent the quick connect or between the quick connect and the L-shaped connector. In one embodiment, the mounting head is polygonal shaped. In one embodiment, the longitudinal axis of the through hole is at an angle of about 20° to 50° from the longitudinal axis of the main body.

Another aspect of the subject disclosure provides a method for removing an implant from a patient that includes positioning the mount over an implant having a shaft implanted within a patient, aligning the longitudinal axis of the mount to be substantially colinear with a longitudinal axis of the implant, inserting a fastener through the through hole of the mount and into the implant, and applying a proximally directed force to the mount.

BRIEF DESCRIPTION OF THE SEVERAL VIEWS OF THE DRAWINGS

The following detailed description of exemplary embodiments of the subject disclosure will be better understood when read in conjunction with the appended drawings. For the purpose of illustrating the present disclosure, there is shown in the drawings exemplary embodiments. It should be understood, however, that the subject application is not limited to the precise arrangements and instrumentalities shown.

DETAILED DESCRIPTION

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1:
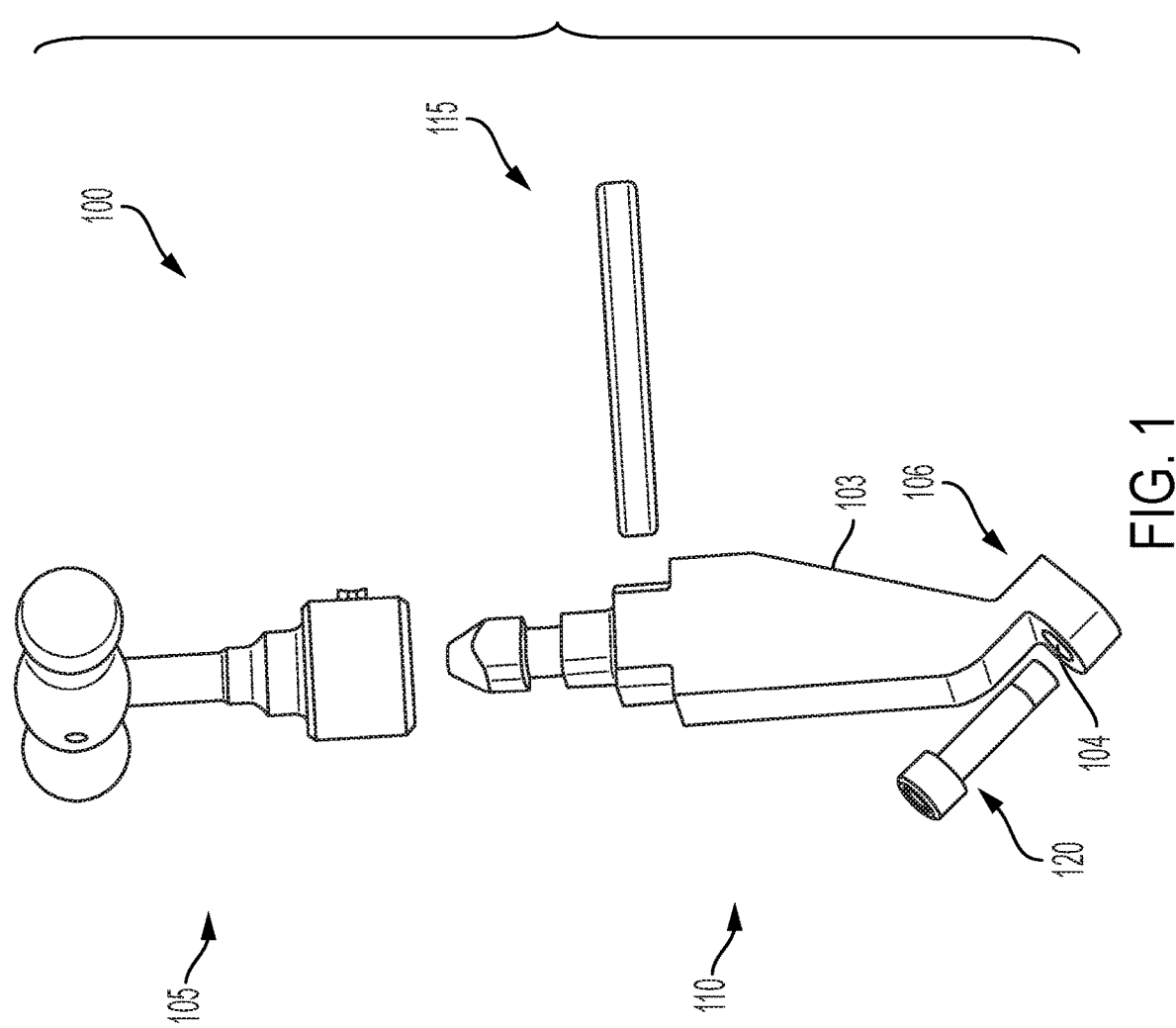
FIG. 1 is a perspective view of an implant extractor assembly in accordance with an exemplary embodiment of the subject disclosure.
Figure 1A:
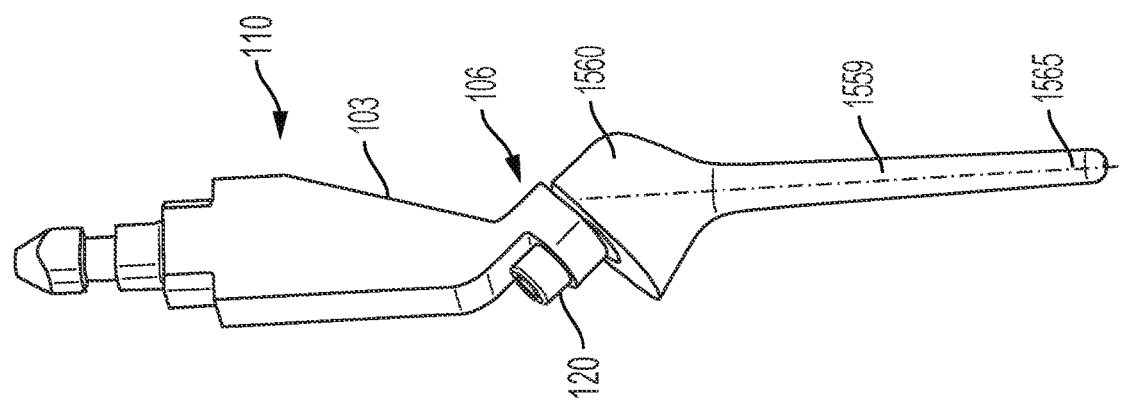
FIG. 1A is a perspective view of the implant extractor assembly of FIG. 1, shown without a strike plate and handle.
Figure 2:
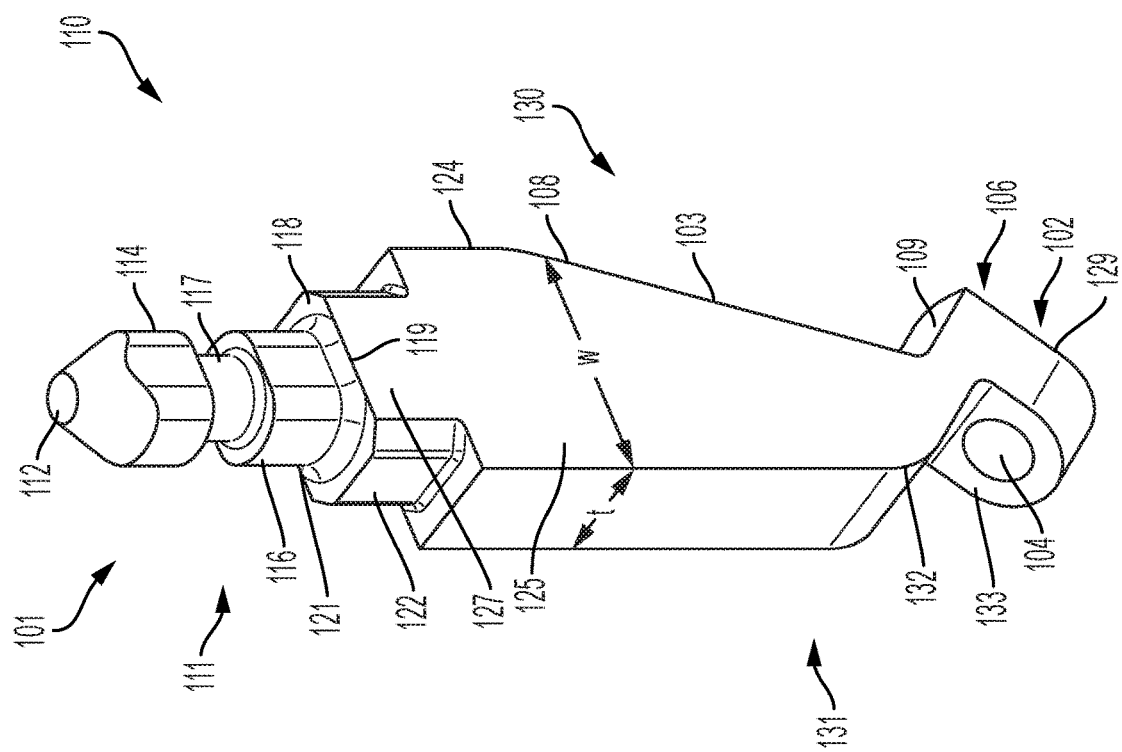
FIG. 2 is a perspective view of a mount of the implant extractor assembly of FIG. 1.
Figure 3:
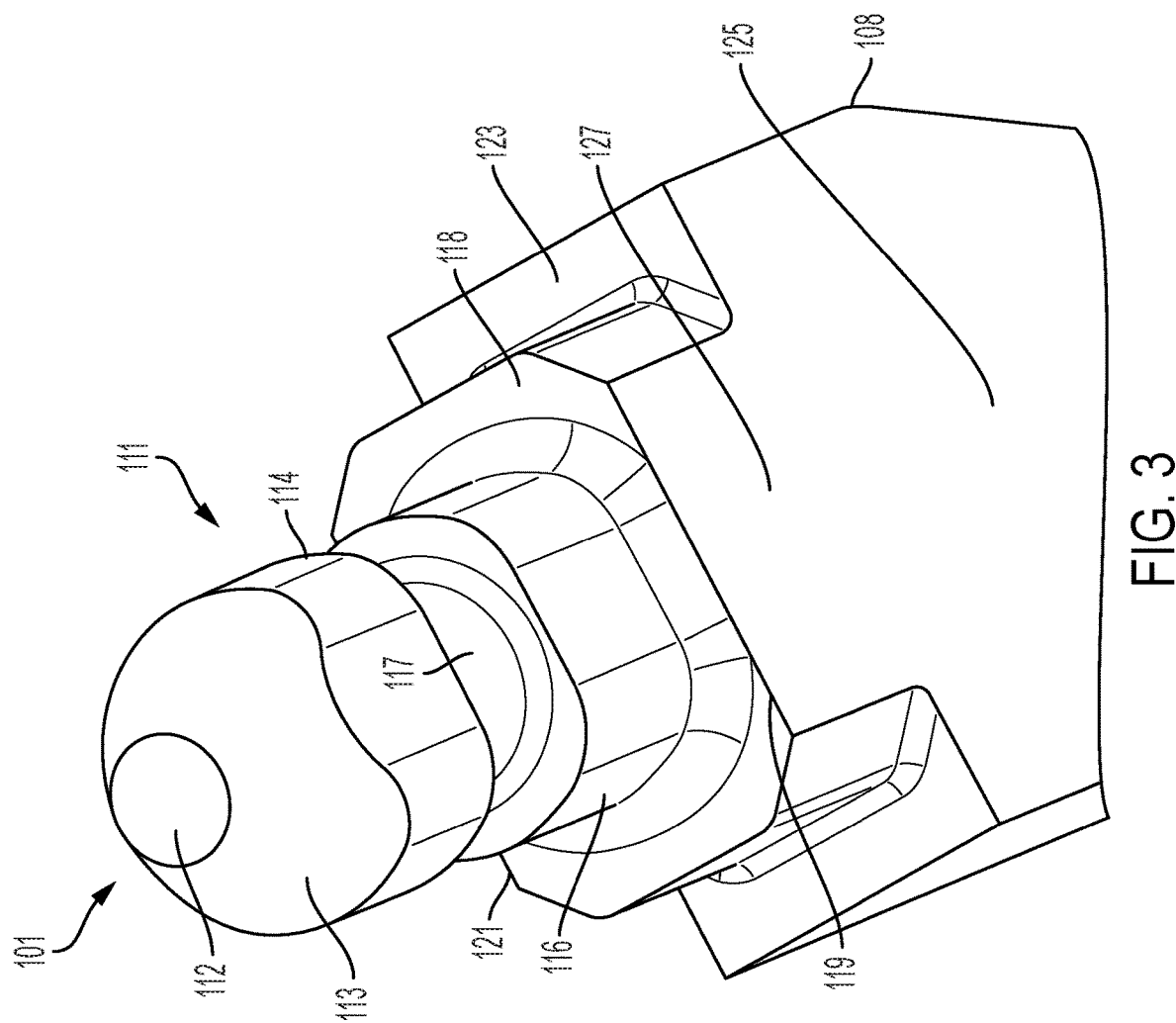
FIG. 3 is an enlarged perspective view of a proximal end of the mount of FIG. 2.
Figure 4:
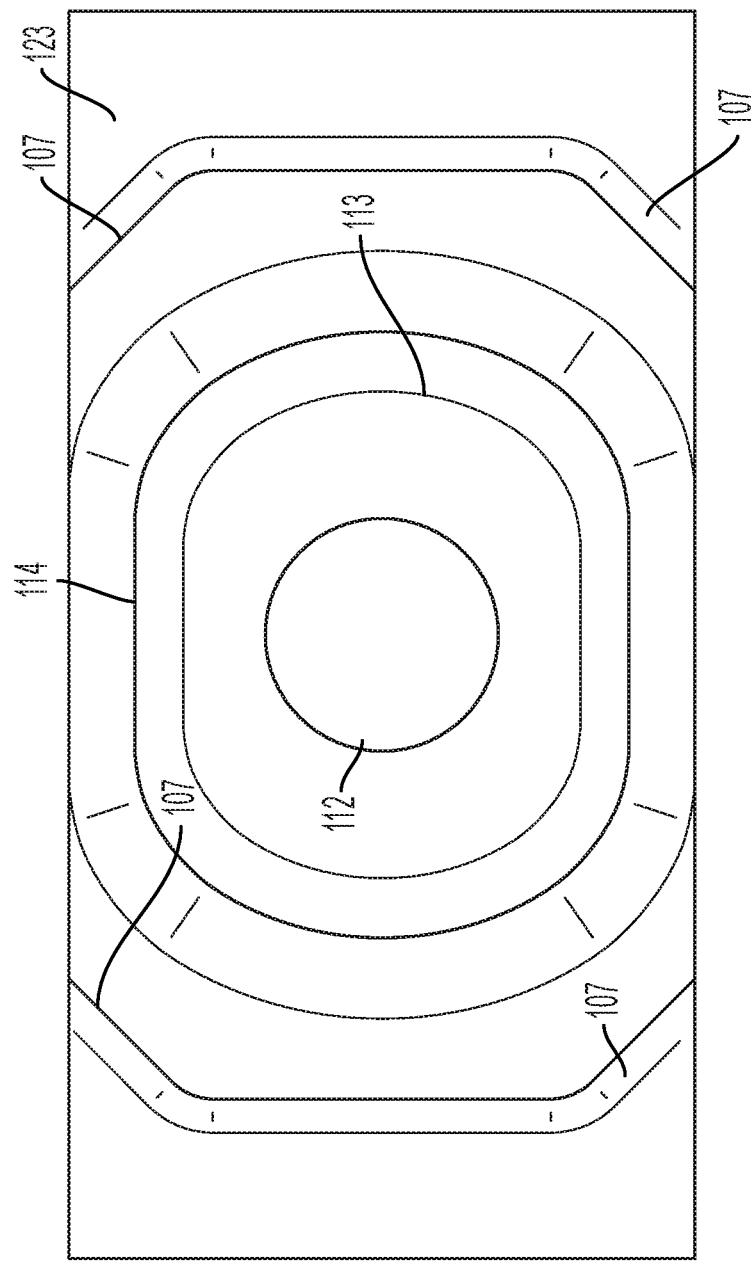
FIG. 4 is a top plan view of the mount of FIG. 2.
Figure 5:
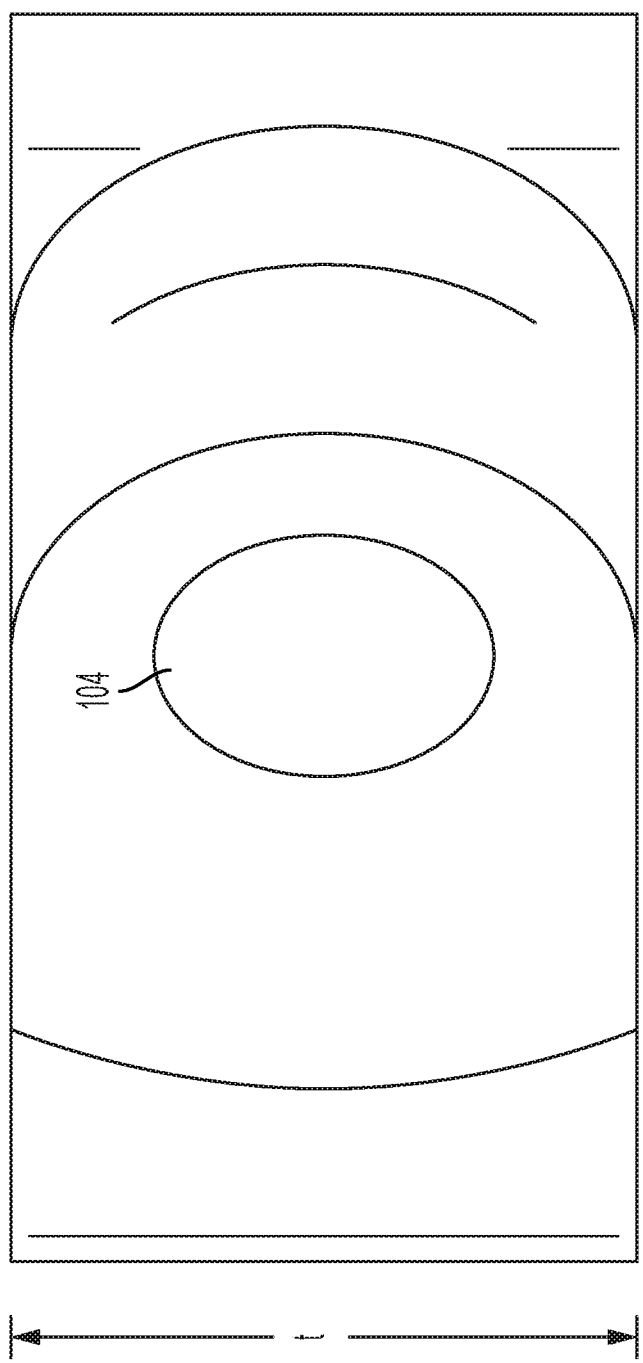
FIG. 5 is a bottom plan view of the mount of FIG. 2.

Referring now to the drawings, FIGS. 1 and 1A depict an implant extractor assembly 100 according to an exemplary embodiment of present disclosure. As shown in FIG. 1, the implant extractor assembly 100 includes a handle 105 and a mount 110 connectable to the handle. In certain embodiments, the implant extractor assembly further includes a strike plate 115 extendable from the mount 110 and/or a fastener 120 that can extend through a through hole 104 of a L-shaped connector 106 of the mount 110. As will be explained below, the implant extractor assembly is adapted to engage an orthopedic implant.

The mount 110 is configured or shown in FIGS. 2-6 and as set forth in greater detail below. The mount includes a quick connect 111 about a proximal end 101 of a main body 103 of the mount. In this illustrative embodiment, the quick connect 111 includes a relatively small circular cross section about the top 112 of the quick connect. A flare 113 extends distally from the top 112 to a first post 114 of the quick connect. The first post 114 has an oval or racetrack cross-sectional shape similar in size and cross-sectional shape to a second post 116 that is co-axial to the first post 114. An annular recess 117 is provided between the first post 114 and the second post 116 having a significantly smaller diameter than first and second posts. In this particular embodiment, the annular recess 117 has an oval or racetrack cross-sectional shape, though other configurations could be provided.

Proceeding in the distal direction from the proximal end 101 to a distal end 102, the second post 116 of the quick connect 111 is mounted or extends from a polygonal shaped block 118. Although other configurations can be provided in accordance with the presently disclosed subject matter, such as block 118 being provided as regular hexagon or regular octagon, the polygonal shaped block 118 in this particular embodiment has an irregular polygonal shape 119 with 8-sides two flats 127, 121 about opposite ends of the block and flats 122. Given the length of the flats 127, 121 the irregular polygonal shape 119 of block 118 in this embodiment can be described as generally having a rectangular shape, with four diagonal edges 107 cutting the four corners of the rectangle (FIG. 4) Flat 127 defines a plane for face 125 of the main body, and flat 121 defines a plane for a second face 126 of the main body, which is opposite face 125.

A plateau 123 extends from a mid-section 124 of the main body 103. In this particular embodiment, the mid-section 124 defines a maximum width, w, of the mount 110 and has a rectangular cross-sectional shape. The polygonal shaped block 118 extends from the top surface of the mid-section defining the shape of the plateau 123. The polygonal shaped block 118 has a maximum width less than a maximum width, W, defined by the mid-section 124. The reduced maximum width of the block 118, as compared to the width w of the mid-section 124 provides the plateau 123 upon which the strike plate 115 seats on or engages.

The shape and configuration of the block 118 and the plateau 123 are provided for purposes of illustration and not limitation. In certain embodiments that include a strike plate, the strike plate 115 is adapted to provide a proper fitting (e.g., aperture) based on block 118 and plateau 123 of the main body 103. The shape and configuration of the block and plateau can vary in other embodiments which do or do not include a strike plate.

A thickness, t, of the midsection 124 and the thickness of the mount 110 in general is provided by the distance between flats 127 and 121. As noted, the mount 110 has a maximum width w at the mid-section 124, and then tapers at taper 108 to provide a reduced distal width as one proceeds toward the L-shaped connector 106, discussed in greater detail below.

Figure 6:
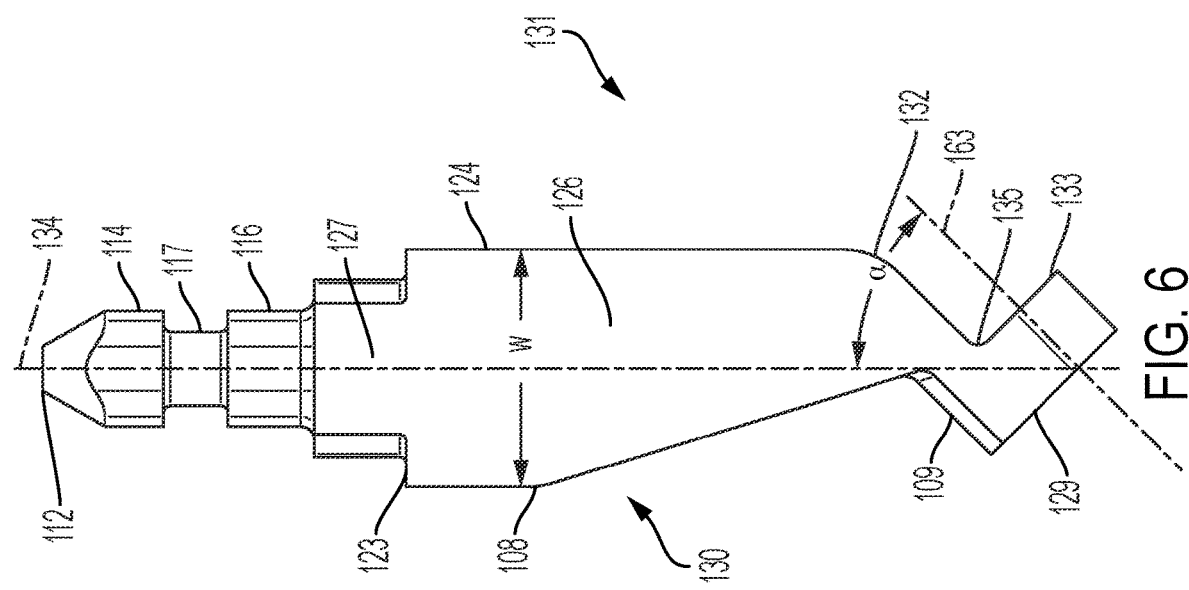
FIG. 6 is a side view of the mount of FIG. 2.

In this particular illustrative embodiment, the main body 103 of the mount 110 continues to taper inward from taper 108 along a side 130 of the mount, at a constant thickness, t, until it reaches at or about the center of the width w defined by the mid-section 124, as best shown in FIG. 6. At this point, the main body 103 flares outward along the side 130 of the mount 110 to form a substantially upwardly or proximally facing face 109 of the L-shaped connector 106 that is angled relative to the longitudinal axis 134 of the mount. In accordance with exemplary aspects of the embodiment the angle of the face 109 can be about 30, 35, 40, 45, 50, 55, or 60 degrees. An engorging face 129 to the L-shaped connector is oriented perpendicularly or substantially perpendicularly from the face 109. In other words, the engorging face 129 faces downwardly about an angle relative to the longitudinal axis 134 of the mount, e.g., about 100, 105, 110, 115, 120, 125, 130, 135, 140, 145, 150, 155, 160, 165, or 170 degrees. The side 131 of the mount opposite side 130 does not taper initially, but then tapers at taper 132 to run generally parallel to the face 109, and is then angled perpendicularly or substantially perpendicular at a vertex 135 of the L-shaped connector to run parallel to the engorging face 129 thereby providing an L-shaped connector 133 having a through hole 104.

As best shown in FIG. 6, the longitudinal axis 134 of the main body 103 extends from the center of top 112 through the center of the quick connect 110, and through the center of the mid-section 124. A central axis 163 of the through hole 104 extending through the center of the through hole 104, and traverses to the longitudinal axis 134 of the main body 103. In certain exemplary embodiments, the central axis 163 of the through hole is at an angle, a, of about 20° to 50° from the longitudinal axis 134 of the main body. In certain embodiments, angle α can range from about 10° to 60°, from about 30° to about 40°, or can be about 20°, 25°, 30°, 35°, 40°, 45°, or 50°±5° or ±2.5° or ±1°.

Figure 7:
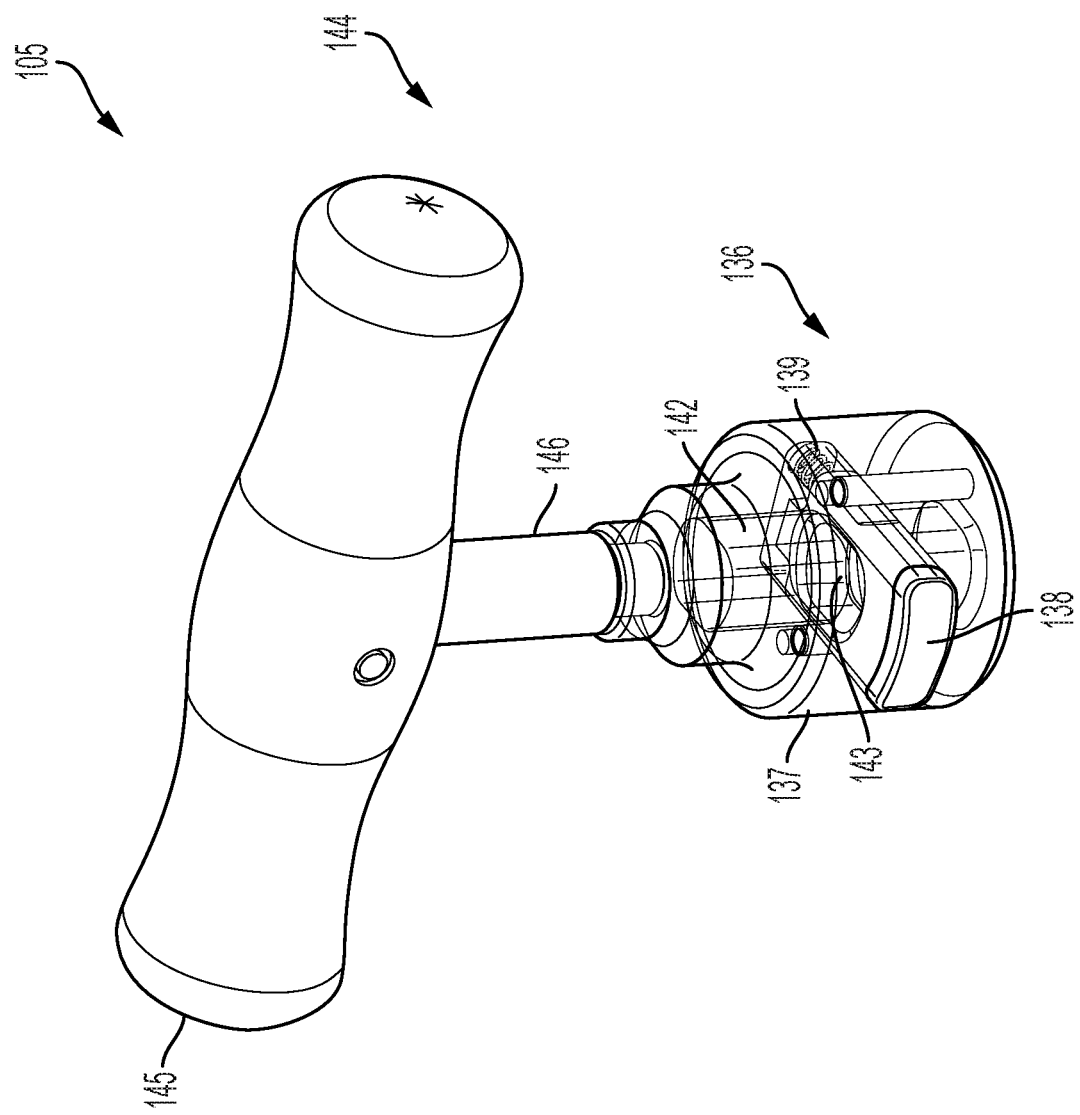
FIG. 7 is a perspective view of an exemplary embodiment of a handle of the implant extractor assembly of FIG. 1.

FIG. 7 depicts a handle 105 that connects with the quick connect 111 about the proximal end 101 of the main body 103 via a cooperating quick connect 136 located about a distal end of the handle. Rendered transparent for purposes of clarity in FIG. 7, a housing 137 surrounds the cooperating quick connect 136 of the handle 105. The cooperating quick connect 136 includes an actuator 138 that is biased by a spring 139 or other biasing mechanism. The actuator contains a racetrack or oval actuator aperture 143. A circular plane 140 is provided about the distal end of the handle, through which an oval or racetrack shaped aperture 141 to a channel 142 with an oval or racetrack cross-sectional shape is provided. The aperture 141, channel 142 and actuator aperture 143 each have a similar cross-sectional shape and are each sized and shaped to receive quick connect 110 of the main body 103.

Figure 8:
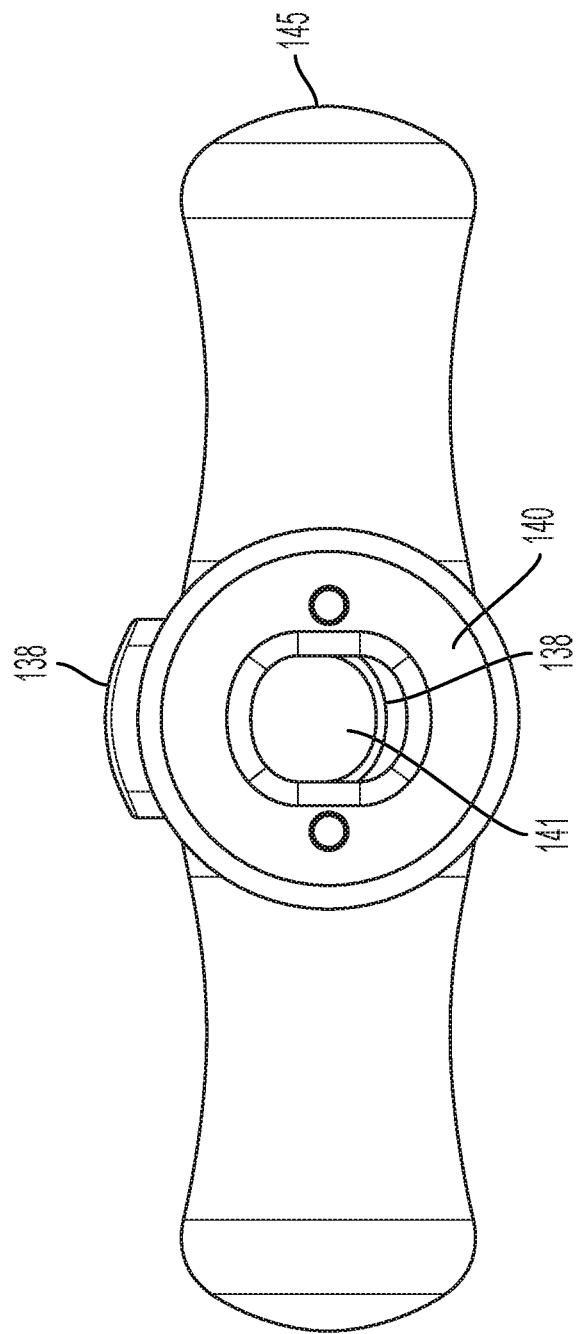
FIG. 8 is a bottom plan view of the handle of FIG. 7.

As best shown in FIG. 8, in the normally biased position, the actuator aperture 143 is not aligned with the channel 142 such that the channel 142 of the cooperating quick connect 136 is partially obstructed by the spring-biased actuator 138. As the quick connect 110 of the main body 103 is inserted into the cooperating quick connect 136 of the handle 105, the flare 113 will advance the actuator aperture against the bias of spring 139 to force the actuator aperture in co-alignment with the channel 142 to accommodate the distally increasing diameter of the quick connect 111. Once the actuator reaches the annular recess 117 of quick connect 111, the actuator is allowed to return to its normally biased position, in which the channel 142 is again partially obstructed. The partially obstructed channel 142 does not allow movement of the mount 110 owing to the relatively larger diameters of the first post 114 and the second post 116 of the quick connect 111, and the handle 105 is locked into place. To remove the handle, the actuator 138 is depressed to co-align the actuator aperture 143 with the channel 142 and allow the first post 114 to clear the actuator 138.

A T-handle 144 is connected to the housing 137 defining the proximal end of the handle 105. In this particular embodiment, the T-handle includes a shaft 146 centered about a gripper 145 adapted to be ergonomically by a user's hand.

Figure 9:
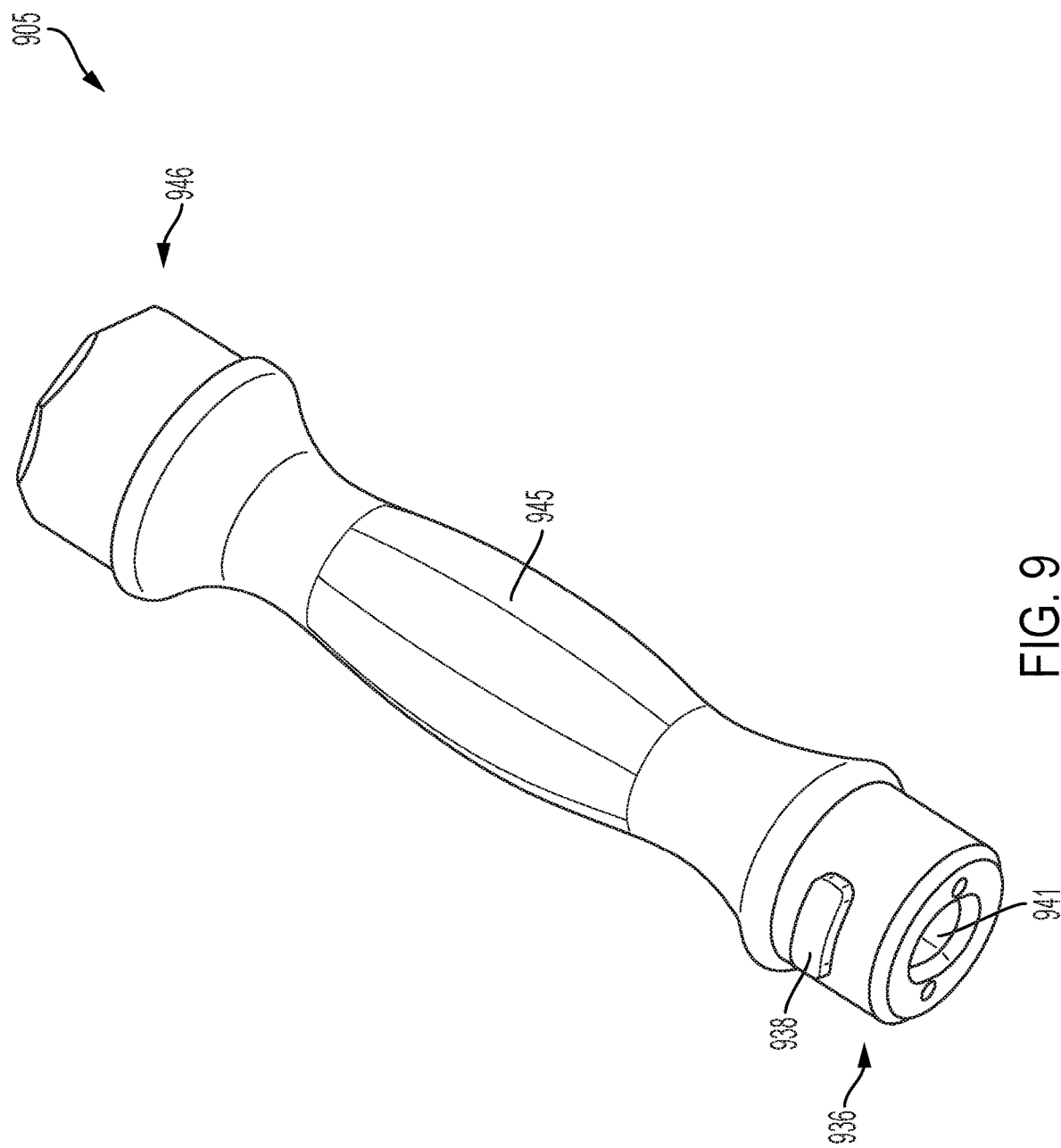
FIG. 9 is perspective view of a handle of the implant extractor assembly according to an exemplary embodiment.

FIG. 9 depicts a handle 905 according to an alternative exemplary embodiment for connection with the mount 110. The handle provides a gripper 945 that is sized and shaped to be ergonomically gripped by at least one hand. The handle 905 contains a cooperating quick connect 936 similar or identical in design to the cooperating quick connect 136 discussed above in FIGS. 7 and 8, the cooperating quick connect 936 also including an actuator 938 and an aperture 941 similar or identical in design to those found on the cooperating quick connect 136.

Figure 10:
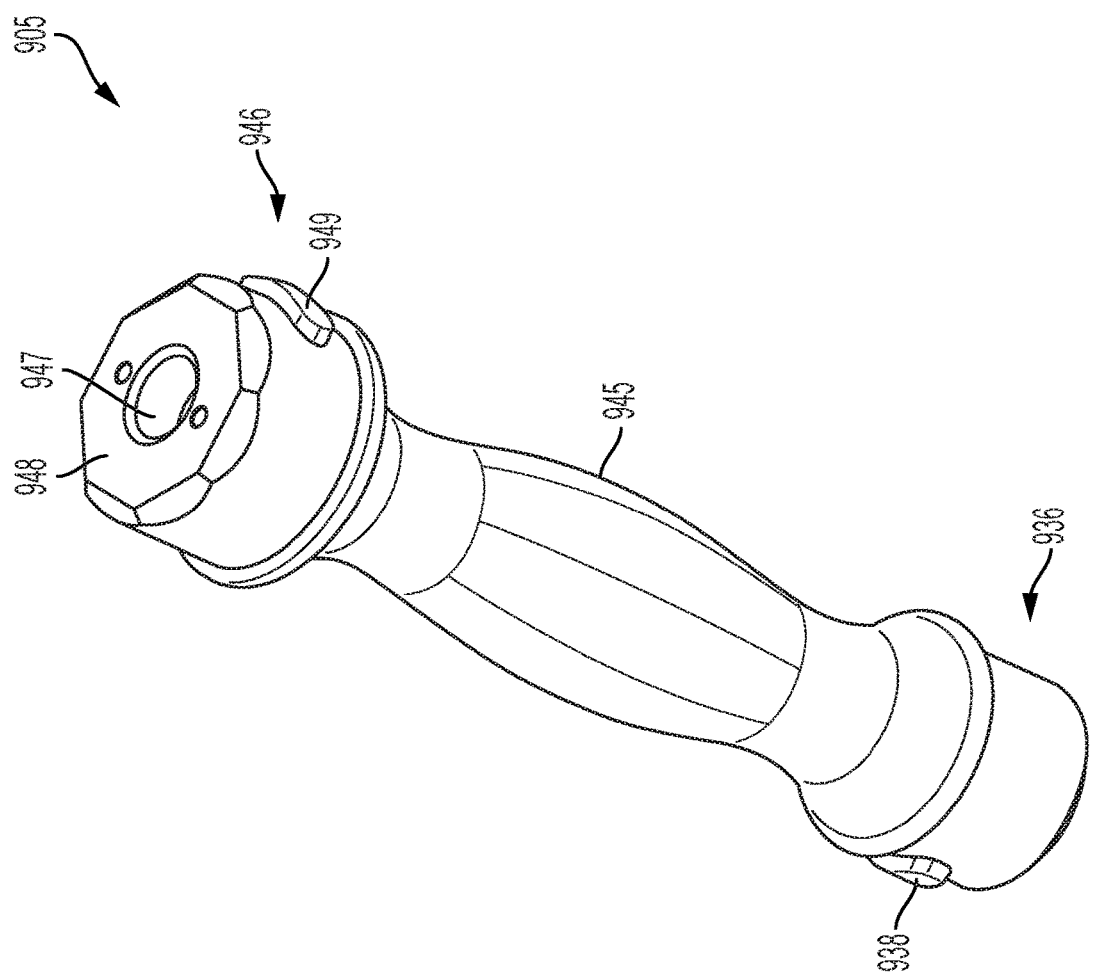
FIG. 10 is another perspective view of the handle of FIG. 9.

As shown in FIG. 10, the handle 905 can in certain embodiments further include a second cooperating quick connect 946 about an end opposite the cooperating quick connect 936, which has a second actuator 949 and a similar design to cooperating quick connect 936. Second cooperating quick connect 946 is distinguished from cooperating quick connect 936 in that it has a circular shaped aperture 947 about a proximal face 948, that forms the aperture 947 to a channel with a circular cross-sectional shape (not shown).

Figure 11:
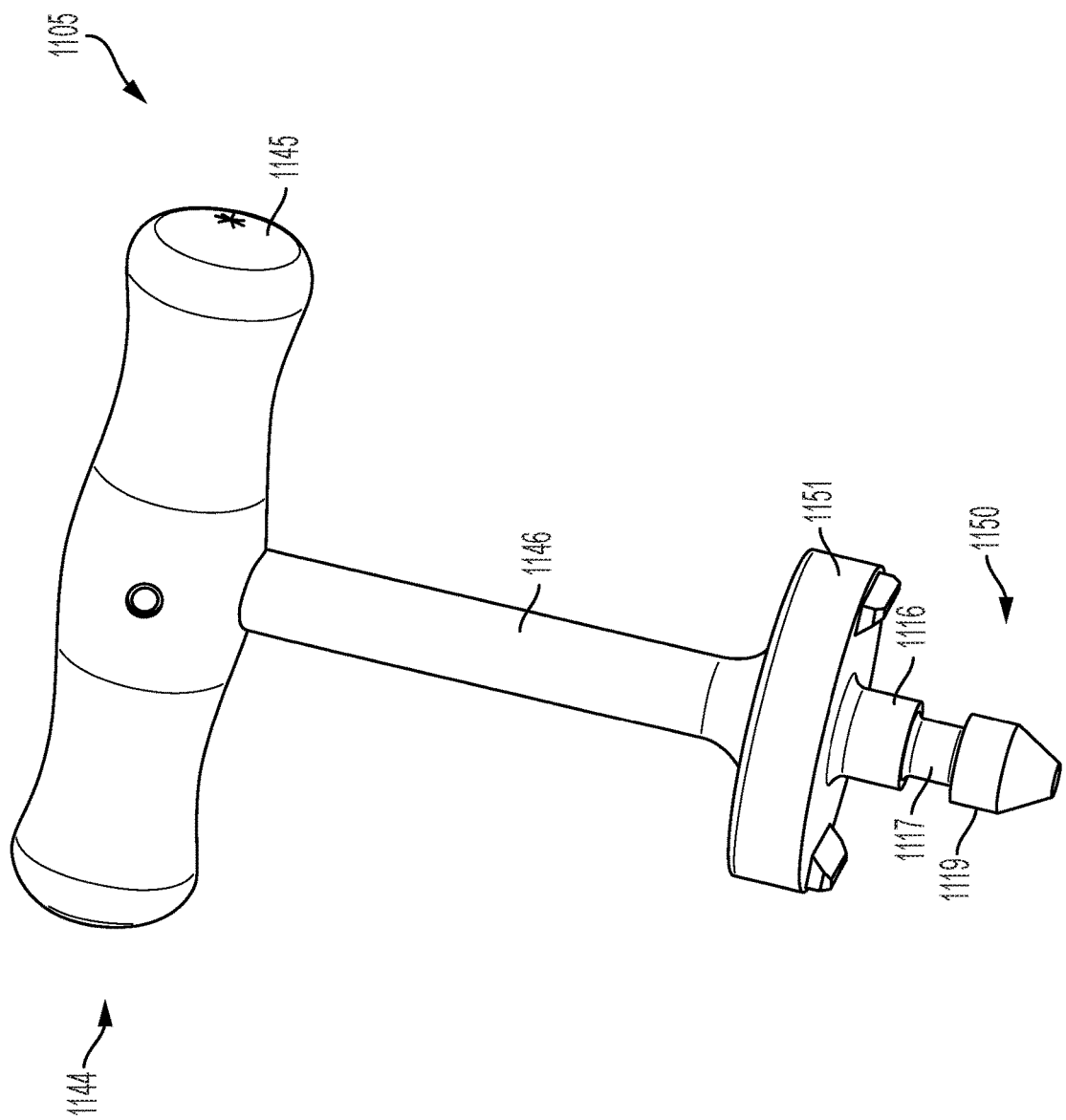
FIG. 11 is a perspective view of a handle of the implant extractor assembly according to yet another exemplary embodiment.

FIG. 11 depicts a handle component 1105 according to another exemplary embodiment that can be used, for example, in conjunction the handle 905. The handle component 1105 includes a T-handle 1144 similar to T-handle 144, having a shaft 146. The handle component 1105 further includes a handle quick connect 1150 similar to quick connect 111 of the main body 103. Handle quick connect 1150, however, includes a first post 1114, a second post 1116, and an annular recess 1117 each having a circular cross-sectional shape. Handle quick connect 1150 can be engaged with the second cooperating quick connect 946 to join handle 905 with handle component 1105. A hub 1151 with a relatively large diameter is provided centrally about, and between, the shaft 1146 and the handle quick connect 1150. Other alternative configurations can be provided in accordance with the subject disclosure.

Figure 12:
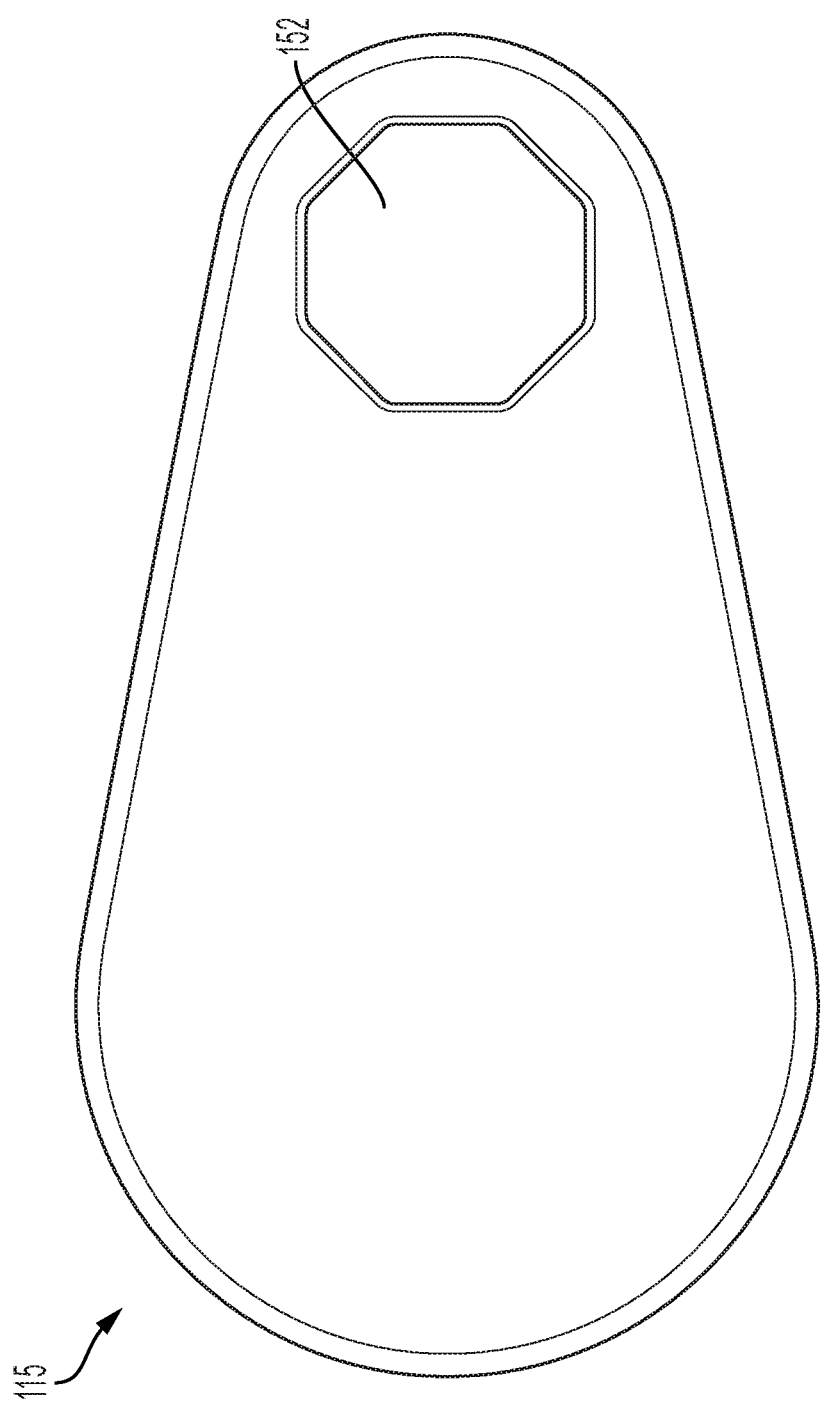
FIG. 12 is a top plan view of an exemplary embodiment of a strike plate of the implant extractor assembly of FIG. 1.
Figure 13:
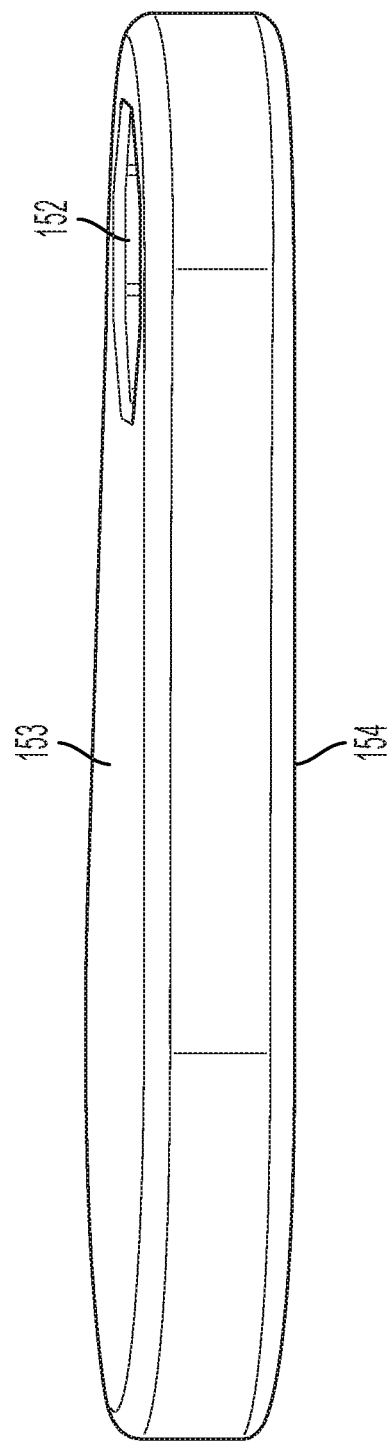
FIG. 13 is a side view of the strike plate of FIG. 12.

In accordance with an exemplary embodiment the strike plate 115 is configured as shown in FIGS. 12 and 13, which can be included in the implant extractor assembly 100 in certain embodiments. The strike plate includes an aperture 152 that has a regular octagonal shape that is sized such that it can be securely connected about the polygonal shaped block 118, which in this embodiment is generally a rectangular shape, with four diagonal edges cutting the four corners of the rectangle. The shape of the polygonal shaped block 118 and the aperture can be modified, so long as the strike plate 115 is secured about the polygonal block 118. The strike plate 115 has a pair of opposite planar faces 153, 154 having an increasing width about en end opposite the aperture 152 as shown in FIG. 12 to provide a surface for striking the strike plate with e.g., a surgical hammer (not shown).

Figure 14:
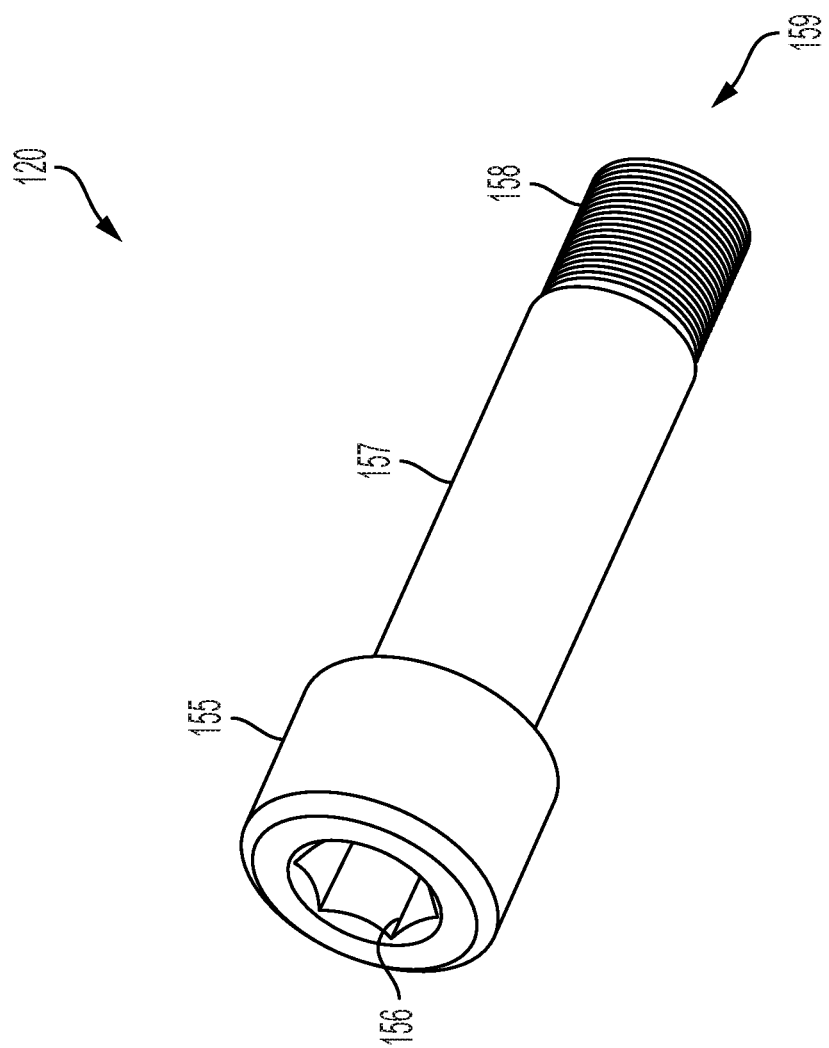
FIG. 14 is a perspective view of an exemplary embodiment of a fastener of the implant extractor assembly of FIG. 1.

FIG. 14 depicts the fastener 120 according to an exemplary embodiment. The fastener 120 includes a socket head 155 that has a diameter larger than the diameter of the through hole 104 of the L-shaped connector. A proximal end 156 to the socket head 155 can include a standard sized socket fitting. A shaft 157 proceeds from the socket head and has a diameter sized to fit or slide through the through hole 104. The shaft 157 can be provided with threading 158 about its distal end 159, and have an overall longitudinal length that can vary depending on the orthopedic implant which is being extracted. The diameter of the shaft, or, in embodiments that do not include a circular shaft, the size of the shaft in general, is based on the diameter or size of an existing anchor hole (e.g., hole 1558, FIG. 15) in the orthopedic implant being extracted. For example, if the existing anchor hole does not contain threading, or if the existing anchor hole has a specific contour, the shaft can be provided without threading, or with a complementary contour, depending on the orthopedic implant being removed. In any event, the shaft 157 is sized to fit securely within the existing anchor hole 1558 of the implant, and in this exemplary embodiment, the threading 158 is complementary to threading provided in the anchor hole.

Figure 15:
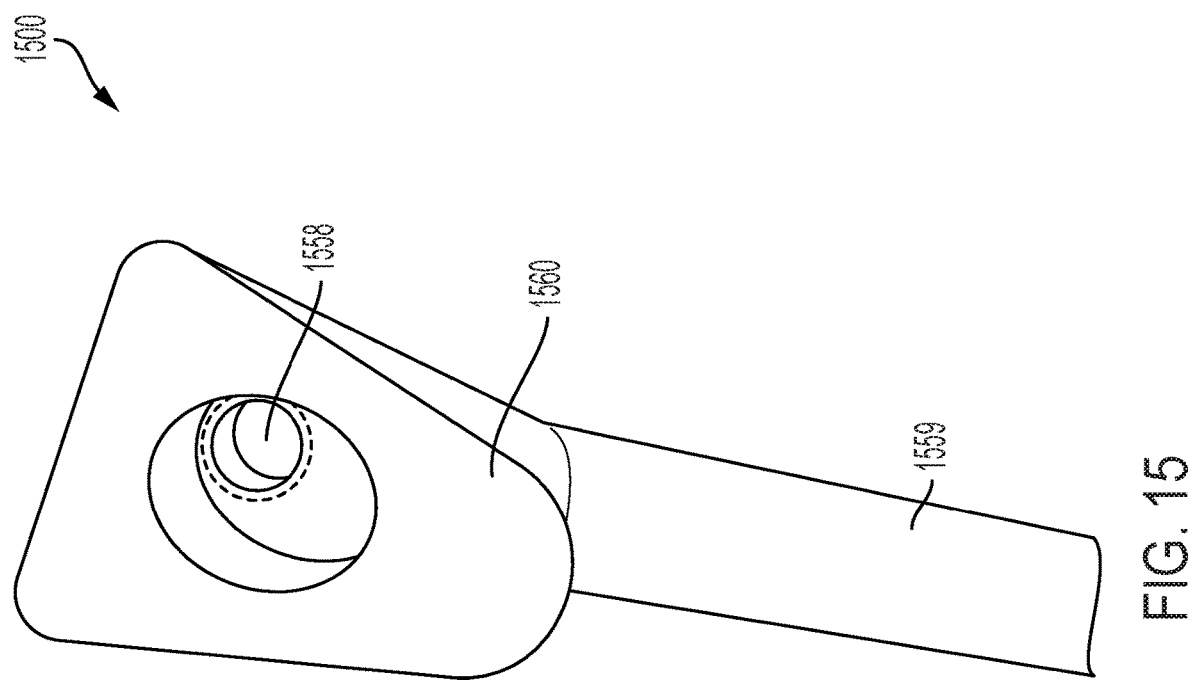
FIG. 15 is a perspective view of an exemplary embodiment of an orthopedic implant.
Figure 16:
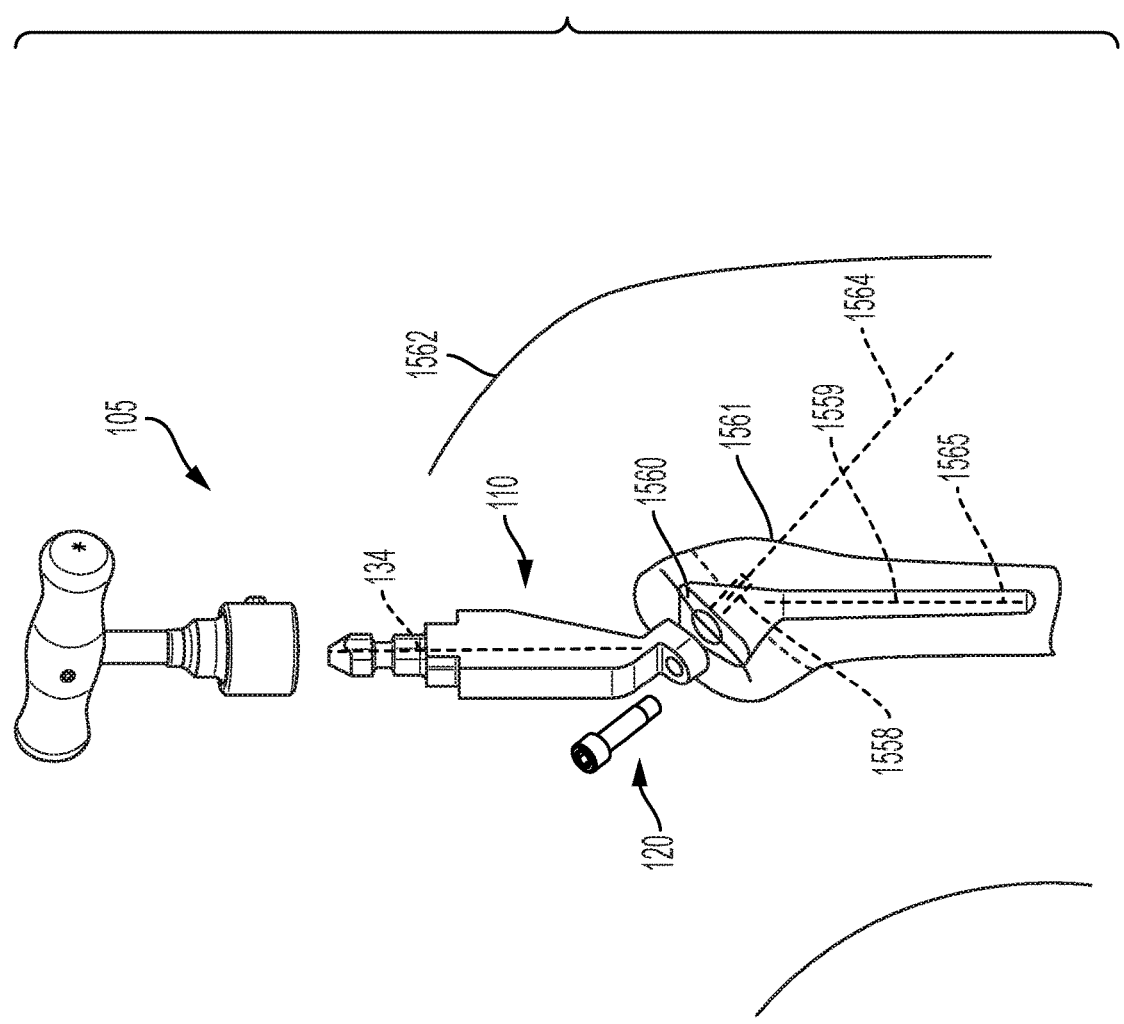
FIG. 16 is a view of the implant extractor assembly of FIG. 1 adjacent a representative implant.

FIGS. 15 and 16 depict an orthopedic implant 1500 to which implant extractor assemblies of the present disclosure can be applied, such as in a revision surgery. The implant 1500 can include a humeral stem 1559 and a humeral head 1560. The humeral head 1560 can be provided with one or more apertures, including the anchor hole 1558, to receive, for example, a polyethylene humeral concavity insert for contact with the glenosphere. The center of the anchor hole 1558 defines a longitudinal axis 1564 of the implant. As depicted in FIGS. 15 and 16, the humeral stem 1559 has been previously inserted into a humerus 1561, and the shoulder area 1562 has been isolated for revision surgery, with the humeral concavity insert having been removed.

In operation, the mount 110 is positioned over the humeral head 1560. The central axis 163 of the through hole is aligned with a central axis 1564 of the implant. So aligned also aligns the longitudinal axis 138 of the mount with the longitudinal axis 1565 of the implant. The fastener 120 is then inserted through the through hole 104 of the mount 110 and into the implant (e.g., into anchor hole 1558). In this position, the longitudinal axis of the mount 134 is colinear, or substantially colinear with a longitudinal axis 1565 of the implant. A proximal force is then applied to the handle 105 to remove the implant 1500. As the longitudinal axis 134 is aligned with e.g. parallel with the longitudinal axis of the implant, the proximally directed force advantageously provides a line of force in a single direction that facilitates removal of the implant from bone.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

The invention claimed is:

1. An implant extractor assembly comprising:
   a handle;
   a mount connectable to the handle, the mount including:
   a main body,
   a quick connect about a proximal end of the main body,
   a mounting block between the main body and the quick connect, and
   an L-shaped connector about a distal end of the main body, the L-shaped connector including a through hole having a longitudinal axis transverse to a longitudinal axis of the main body; and
   a strike plate configured to matingly engage and circumscribe the mounting block and for being struck by a striking tool.

2. The implant extractor assembly of claim 1, wherein the through hole is positioned along the longitudinal axis of the main body.

3. The implant extractor assembly of claim 1, further comprising a fastener for extending through the though hole.

4. The implant extraction assembly of claim 1, wherein the longitudinal axis of the through hole is at an angle of about 20° to 50° from the longitudinal axis of the main body.

5. The implant extractor assembly of claim 1, wherein the strike plate extends substantially perpendicular to the longitudinal axis of the main body.

6. The implant extractor assembly of claim 1, wherein the mounting block includes a pair of opposing flats adjacent the quick connect for engaging the strike plate.

7. The implant extractor assembly of claim 1, wherein the main body includes a plateau for engaging the strike plate.

8. The implant extractor assembly of claim 1, wherein the mounting block is configured to receive the strike plate.

9. The implant extractor assembly of claim 8, wherein the mounting block is polygonal shaped.

10. The implant extractor assembly of claim 1, wherein a longitudinal axis of the handle is parallel to the longitudinal axis of the main body.

11. The implant extractor assembly of claim 1, wherein a longitudinal axis of the handle is coaxial to the longitudinal axis of the main body.

12. The implant extractor assembly of claim 1, wherein the handle includes a cooperating quick connect for operatively engaging the quick connect of the main body.

13. The implant extractor of claim 1, wherein the main body includes the proximal end having an overall width greater than the distal end of the main body.

14. The implant extractor of claim 1, wherein the main body includes a first lateral side that extends substantially parallel to a central longitudinal axis of the main body and a second lateral side that tapers from the proximal end to the distal end of the main body.

15. The implant extractor assembly of claim 1, wherein the mounting block has an overall width larger than an overall width of the quick connect.

16. A mount for an implant extractor assembly, the mount comprising:
    a main body;
    a quick connect about a proximal end of the main body;
    a mounting block between the main body and the quick connect, wherein a proximal end of the main body defines a flange extending from the mounting block;
    an L-shaped connector about a distal end of the main body, the L-shaped connector including a through hole having a longitudinal axis transverse to a longitudinal axis of the main body; and
    a strike plate configured to matingly engage and circumscribe the mounting block and for being struck by a striking tool.

17. The mount of claim 16, wherein the mounting block is adjacent to the quick connect.

18. The mount of claim 16, wherein the mounting block is between the quick connect and the L-shaped connector.

19. The mount of claim 18, wherein the mounting block is polygonal shaped.

20. The mount of claim 16, wherein the longitudinal axis of the through hole is at an angle of about 20° to 50° from the longitudinal axis of the main body.

21. A method for removing an implant from a patient comprising:
    positioning the mount of claim 16 over an implant having a shaft implanted within a patient;
    aligning the longitudinal axis of the through hole of the mount to be substantially colinear with a longitudinal axis of the implant;
    inserting a fastener through the through hole of the mount and into the implant; and
    applying a proximally directed force to the mount.

22. The mount of claim 16, wherein the mounting block has an overall width that is larger than an overall height of the mounting block, and wherein the flange extends substantially perpendicular to a lateral side of the mounting block.

23. An implant extractor assembly comprising:
    a handle; and
    a mount connectable to the handle, the mount including:
    a main body having a proximal end having an overall width greater than a distal end of the main body,
    a quick connect about the proximal end of the main body,
    a mounting block configured to matingly engage a correspondingly configured tool, and
    an L-shaped connector about the distal end of the main body, the L-shaped connector including a through hole having a longitudinal axis transverse to a longitudinal axis of the main body.

24. An implant extractor assembly comprising:
    a handle; and
    a mount connectable to the handle, the mount including:
    a main body having a first lateral side that extends substantially parallel to a central longitudinal axis of the main body and a second lateral side that tapers from a proximal end to a distal end of the main body,
    a quick connect about the proximal end of the main body,
    a mounting block configured to matingly engage a correspondingly configured tool, and
    an L-shaped connector about the distal end of the main body, the L-shaped connector including a through hole having a longitudinal axis transverse to a longitudinal axis of the main body.

\* \* \* \* \*